US010575735B2

(12) United States Patent
Suwa

(10) Patent No.: US 10,575,735 B2
(45) Date of Patent: Mar. 3, 2020

(54) OBJECT INFORMATION ACQUIRING APPARATUS

(71) Applicant: CANON KABUSHIKI KAISHA, Tokyo (JP)

(72) Inventor: Takeshi Suwa, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 432 days.

(21) Appl. No.: 15/367,324

(22) Filed: Dec. 2, 2016

(65) Prior Publication Data

US 2017/0181637 A1 Jun. 29, 2017

(30) Foreign Application Priority Data

Dec. 24, 2015 (JP) ................................ 2015-250981

(51) Int. Cl.
*A61B 5/00* (2006.01)

(52) U.S. Cl.
CPC .......... *A61B 5/0095* (2013.01); *A61B 5/4312* (2013.01); *A61B 5/708* (2013.01); *A61B 5/7203* (2013.01); *A61B 5/7217* (2013.01); *A61B 5/7225* (2013.01)

(58) Field of Classification Search
CPC ........................................................ A61B 5/00
See application file for complete search history.

(56) References Cited

U.S. PATENT DOCUMENTS 9,857,215 B2 1/2018 Abe
2012/0146454 A1* 6/2012 Fujii ..................... B06B 1/0292 310/300
2013/0205903 A1* 8/2013 Oyama ................ A61B 5/0095 73/596
2014/0187903 A1* 7/2014 Oyama ................ A61B 5/6852 600/407
2015/0099973 A1* 4/2015 Abe .................. G01N 21/1702 600/440

(Continued)

FOREIGN PATENT DOCUMENTS

JP 2007-159781 A 6/2007
JP 2010-240131 A 10/2010

(Continued)

OTHER PUBLICATIONS

Office Action dated Sep. 3, 2019, in counterpart application JP 2015-250981 (7 pages).

(Continued)

*Primary Examiner* — Joel F Brutus
(74) *Attorney, Agent, or Firm* — Venable LLP

(57) ABSTRACT

An object information acquiring apparatus according to the present invention includes: an acoustic wave detecting element which detects an acoustic wave propagating from an object and which outputs an acoustic signal; a reference element which receives an input of electrical noise corresponding to electrical noise input to the acoustic wave detecting element and which outputs a reference signal; a noise reducer which reduces a component derived from the electrical noise by subtracting the reference signal from the acoustic signal; and a processor which generates image data representing characteristic information of the object using the acoustic signal in which the component derived from the electrical noise has been reduced.

19 Claims, 11 Drawing Sheets

(56) References Cited

U.S. PATENT DOCUMENTS

| | | | | |
|---|---|---|---|---|
| 2015/0268091 | A1* | 9/2015 | Abe | G01H 11/06 367/181 |
| 2018/0080813 | A1 | 3/2018 | Abe | |

FOREIGN PATENT DOCUMENTS

| | | |
|---|---|---|
| JP | 2011-200381 | 10/2011 |
| JP | 2015-177907 A | 10/2015 |
| JP | 2016-163608 A | 9/2016 |

OTHER PUBLICATIONS

Machine English Translation of JP 2016-163608 (published Sep. 8, 2016)(32 pages).
Machine English Translation of JP 2007-159781 (published Jun. 28, 2007)(15 pages).
Machine English Translation of JP 2010-240131 (published Oct. 28, 2010)(30 pages).
Machine English Translation of JP 2015-177907 (published Oct. 8, 2015)(46 pages).

* cited by examiner

OBJECT INFORMATION ACQUIRING APPARATUS

BACKGROUND OF THE INVENTION

Field of the Invention

The present invention relates to an object information acquiring apparatus.

Description of the Related Art

There is technology called photoacoustic tomography (PAT) which involves irradiating an object section with pulsed light generated by a light source and, using a photoacoustic effect in which an acoustic wave is generated by absorption of light inside the object section, imaging internal tissue that acts as a generation source of an acoustic wave. Proposals are being made to utilize this technology for imaging of physiological information (in other words, functional information) of a living organism.

Generally, an electrical signal acquired from an acoustic wave detecting element in photoacoustic tomography contains, in addition to a signal attributable to an acoustic wave generated from inside a living organism, electrical noise propagated by capacity coupling with a metallic member of a case, a ground line, or the like. Examples of electrical noise include switching noise of a direct-current switching power supply. In addition, when an apparatus is provided with a stepping motor or the like, a large amount of electrical noise tends to be generated by the motor and peripheral circuits thereof when a drive coil is energized by an input of a control signal or by switching. In order to obtain a diagnostic image with good quality, the effect of such electrical noise on the image must be reduced.

With respect to this problem, Japanese Patent Application Laid-open No. 2011-200381 describes a noise reduction method in a system including a plurality of motors, peripheral circuits thereof, and an acoustic wave detecting element. FIGS. 9A and 9B are diagrams showing examples of an electrical signal output from a probe, in which FIG. 9A represents a state during operation of a motor and FIG. 9B represents a state during stoppage of the motor. In Japanese Patent Application Laid-open No. 2011-200381, at least a part of the operation of the motor is stopped during a period where the acoustic wave detecting element receives an acoustic wave. Accordingly, a signal of the acoustic wave detecting element makes a transition from a state where the signal includes electrical noise of the motors and peripheral circuits thereof as shown in FIG. 9A to a state where the signal does not include electrical noise of the motors and peripheral circuits thereof as shown in FIG. 9B.

Patent Literature 1: Japanese Patent Application Laid-open No. 2011-200381

SUMMARY OF THE INVENTION

When an acoustic wave detecting element is controlled so that a movement locus of the acoustic wave detecting element assumes a complex and smooth locus such as that of a true circle or a spiral, accuracy of positional control of the acoustic wave detecting element must be increased. In this case, the motor and peripheral circuits thereof such as a linear scale must be frequently energized. However, with a method in which the motor and peripheral circuits thereof are stopped in some periods as described in Japanese Patent Application Laid-open No. 2011-200381, it is difficult to achieve control which enables a complex and smooth locus as described above to be attained. In addition, when a switching power supply is used to control the apparatus, it is difficult to create a period in which the switching power supply is shut down.

The present invention has been made in consideration of the problems described above. An object of the present invention is to reduce, in an apparatus which acquires an acoustic wave propagating from an object using an acoustic wave detecting element to acquire internal information, an effect of electrical noise included in an electrical signal from the acoustic wave detecting element.

The present invention provides an object information acquiring apparatus, comprising:

an acoustic wave detecting element which detects an acoustic wave propagating from an object and which outputs an acoustic signal;

a reference element which receives an input of electrical noise corresponding to electrical noise input to the acoustic wave detecting element and which outputs a reference signal;

a noise reducer which reduces a component derived from the electrical noise by subtracting the reference signal from the acoustic signal; and a processor which generates image data representing characteristic information of the object using the acoustic signal in which the component derived from the electrical noise has been reduced.

The present invention also provides an object information acquiring apparatus, comprising:

a pair of acoustic wave detecting elements with mutually different sensitivities with respect to an acoustic wave propagated from an object;

a difference processor which performs difference processing on a pair of electrical signals output from the pair of acoustic wave detecting elements and which outputs a differential signal; and a processor which generates image data representing characteristic information of the object using the differential signal.

According to the present invention, in an apparatus which acquires an acoustic wave propagating from an object using an acoustic wave detecting element to acquire internal information, an effect of electrical noise included in an electrical signal from the acoustic wave detecting element can be reduced.

Further features of the present invention will become apparent from the following description of exemplary embodiments with reference to the attached drawings.

DESCRIPTION OF THE EMBODIMENTS

Figure 1:
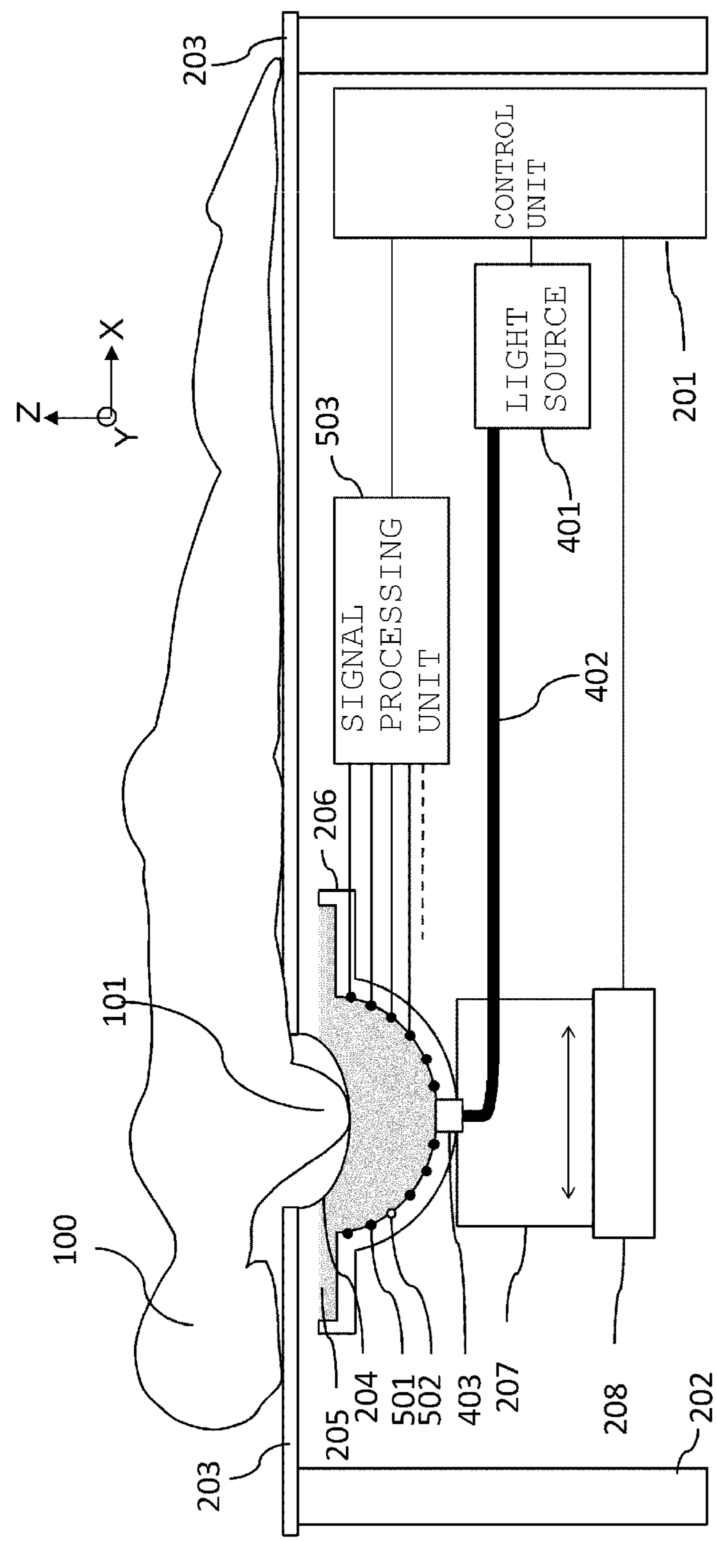
FIG. 1 is an overall configuration diagram of a first embodiment.

Hereinafter, preferred embodiments of the present invention will be described with reference to the drawings. However, it is to be understood that dimensions, materials, shapes, relative arrangements, and the like of components described below are intended to be changed as deemed appropriate in accordance with configurations and various conditions of apparatuses to which the present invention is to be applied. Therefore, the scope of the present invention is not intended to be limited to the embodiments described below.

The present invention relates to a technique for detecting an acoustic wave propagating from an object and generating and acquiring characteristic information of the inside of the object. Accordingly, the present invention can be considered an object information acquiring apparatus or a control method thereof, or an object information acquiring method and a signal processing method. The present invention can also be considered a program that causes an information processing apparatus including hardware resources such as a CPU and a memory to execute these methods or a storage medium storing the program.

The object information acquiring apparatus according to the present invention includes an apparatus utilizing a photoacoustic effect in which an acoustic wave generated inside an object by irradiating the object with light (an electromagnetic wave) is received and characteristic information of the object is acquired as image data. In this case, characteristic information refers to information on a characteristic value corresponding to each of a plurality of positions inside the object which is generated using a received signal obtained by receiving a photoacoustic wave.

Characteristic information acquired by photoacoustic measurement is a value reflecting an absorption rate of optical energy. For example, characteristic information includes a generation source of an acoustic wave generated by light irradiation, initial sound pressure inside an object, an optical energy absorption density or an absorption coefficient derived from initial sound pressure, or a concentration of substances constituting tissue. In addition, a distribution of oxygen saturation can be calculated by obtaining a concentration of oxygenated hemoglobin and a concentration of reduced hemoglobin as concentrations of substances. Furthermore, a glucose concentration, a collagen concentration, a melanin concentration, a volume fraction of fat or water, and the like are also obtained.

The object information acquiring apparatus according to the present invention includes an apparatus using ultrasonic echo technology which transmits an ultrasonic wave to an object, receives a reflected wave (an echo wave) that is reflected inside the object, and acquires object information as image data. In the case of an apparatus using ultrasonic echo technology, the acquired object information is information reflecting a difference in acoustic impedances among tissues inside the object.

A two-dimensional or three-dimensional characteristic information distribution is obtained based on characteristic information at each position in the object. Distribution data may be generated as image data. Characteristic information may be obtained as distribution information of respective positions inside the object instead of as numerical data. In other words, distribution information such as a distribution of initial sound pressure, a distribution of energy absorption density, a distribution of absorption coefficients, and a distribution of oxygen saturation may be obtained.

An acoustic wave according to the present invention is typically an ultrasonic wave and includes an elastic wave which is also referred to as a sonic wave or an acoustic wave. An electrical signal converted from an acoustic wave by a probe or the like is also referred to as an acoustic signal. However, descriptions of an ultrasonic wave or an acoustic wave in the present specification are not intended to limit wavelengths of such elastic waves. An acoustic wave generated by a photoacoustic effect is referred to as a photoacoustic wave or an optical ultrasonic wave. An electrical signal derived from a photoacoustic wave is also referred to as a photoacoustic signal.

In principle, in the following description and in the drawings, a same component will be denoted by a same reference character and a detailed explanation will be omitted. In the following description, as an example of an object information acquiring apparatus, a photoacoustic apparatus which acquires characteristic information inside an object by photoacoustic tomography and which performs imaging will be explained. In addition, in the following description, while a breast of a living organism will be explained as a representative example of an object, an object is not limited thereto and may also include a hand, a foot, and the like. Furthermore, non-living material such as a phantom can also be measured.

<First Embodiment>

An embodiment to which the present invention is applied will be described using an overall configuration diagram of a first embodiment of the present invention shown in FIG. 1.

(Apparatus Configuration)

In FIG. 1, reference numeral 100 denotes an examinee and reference numeral 101 denotes an object section (in this case, a breast) that is an object of examination. In FIG. 1, an X axis, a Y axis, and a Z axis are defined as illustrated. The X axis and the Y axis are horizontal directions. In addition, the Z axis is a height direction.

Reference numeral 201 denotes a control unit which controls the entire apparatus. Specifically, the control unit is preferably a processing circuit or an information processing apparatus which includes a CPU and a memory and which operates in accordance with an instruction such as a program. However, the control unit is not limited to the above.

Reference numeral 203 denotes a bed which supports the examinee 100 in a face-down posture. The bed 203 includes an opening for inserting the object section 101 and a bed leg 202 for maintaining height of the bed 203.

Reference numeral 204 denotes a holding unit for holding the object section 101. Specifically, a material with an acoustic impedance close to that of a human body is favorable. In addition, by reducing thickness of the holding unit 204, reflection by an interface of the object section 101 and the holding unit 204 can be suppressed. Furthermore, with an apparatus using a photoacoustic effect, since the object section 101 is irradiated with light through the holding unit 204, a material with high light transmittance (favorably, 90% or higher) is preferably used for the holding unit 204. Moreover, a material with high rigidity is favorable which does not break even when thin. Examples of preferable materials satisfying these conditions include polymethylpentene and polyethylene terephthalate.

Reference numeral 205 denotes an acoustic matching liquid for propagating an acoustic wave from the object section 101. Specifically, a material must be selected of which an acoustic impedance is close to that of a human body and of which attenuation of an acoustic wave is small. For example, water or oil is favorable.

Reference numeral 206 denotes a supporter which supports the acoustic matching liquid and the like. Specifically, a structure is provided in which a space between the holding unit 204 and the supporter 206 is filled with the acoustic matching liquid 205. The supporter 206 also supports the acoustic wave detecting element.

Reference numeral 207 denotes a supporting stand including an operating mechanism that is used when moving the supporter 206 in a horizontal direction. Specifically, the supporter 206 is two-dimensionally moved in the horizontal direction by combining two rails with one-dimensional directions.

Reference numeral 208 denotes a supporter driving unit which moves the supporter 206 in the horizontal direction. Specifically, the supporter driving unit 208 includes a motor and moves the supporter 206 in the horizontal direction. However, any kind of supporter driving unit may be used as long as the supporter 206 is relatively moved. The supporting stand 207 and the supporter driving unit 208 correspond to a mover according to the present invention.

Reference numeral 401 denotes a light source which generates pulsed light. Specifically, a Ti:Sa laser is preferable. However, the light source is not limited thereto. When the object section 101 is a living organism, a pulse width of the pulsed light generated by the light source 401 is preferably around 10 to 50 nanoseconds. In addition, desirably, a wavelength of the pulsed light is a wavelength which enables light to propagate to the inside of the object section. A specific example of a wavelength range is 600 nm or more and 1100 nm or less which represent wavelengths at which absorption of hemoglobin and water is low.

On the other hand, when a laser is used as the light source 401, a maximum value of irradiation density (an amount of irradiation light per unit area) by which a living organism is irradiated must be prevented from exceeding laser safety standards. Examples of laser safety standards include a maximum permissible exposure (MPE) defined in JIS standard C6802 and IEC 60825-1. Therefore, in order to increase signal intensity, the amount of irradiation light must be increased to the greatest extent feasible within a range that does not exceed MPE.

Reference numeral 402 denotes a light transmitting unit which transmits pulsed light generated by the light source 401. Specifically, a fiber bundle can be preferably used.

Reference numeral 403 denotes a light irradiating unit for irradiating the object section 101 with pulsed light. The light irradiating unit 403 diffuses light exiting an emitting unit of the light transmitting unit 402 using a diffuser plate or a lens (not shown) and irradiates the holding unit 204 and the object section 101 with the diffused light. The light irradiating unit 403 is held by the supporter 206 and moves in the horizontal direction together with a movement of the supporter 206.

Reference numeral 501 denotes an acoustic wave detecting element which detects an acoustic wave from the object section 101 via the acoustic matching liquid 205 and which converts the acoustic wave into an electrical signal. Desirably, the acoustic wave detecting element has high sensitivity and a wide frequency band. Specific examples include those using a piezoelectric element or a capacitive micromachined ultrasonic transducer (CMUT). However, the acoustic wave detecting element is not limited to the above. In addition, attenuation of an acoustic wave can be reduced by filling a space between the acoustic wave detecting element 501 and the holding unit 204 with the acoustic matching liquid 205.

In this case, a plurality of the acoustic wave detecting elements 501 are installed on a surface (inner circumferential surface) in contact with the acoustic matching liquid 205 of the supporter 206 so as to encircle the holding unit 204. In addition, the plurality of acoustic wave detecting elements 501 are installed so that directions (directivity axes) in which a sensitivity of respective reception directivities is highest intersect with each other. When the acoustic wave detecting elements 501 are arranged in this manner, a point where reception directivities of the acoustic wave detecting elements 501 intersect each other has highest resolution. In the present invention, a region with high resolution in a vicinity of a point constituting a region with highest resolution is defined as a high resolution region. For example, a region with a resolution of 70% or higher as compared to the point with highest resolution can be defined as the high resolution region.

Since the high resolution region is a point where reception directivities of the plurality of acoustic wave detecting elements 501 intersect each other, when the acoustic wave detecting elements 501 are fixed to the supporter 206, spatial positions relative to the supporter 206 are fixed. Therefore, in order to measure a region that is larger than the high resolution region, the supporter 206 must be moved.

Reference numeral 502 denotes an electrical noise detecting element which has a similar electrical configuration to the acoustic wave detecting element 501 and which is used to detect electrical noise input to the acoustic wave detecting element 501. Specifically, acoustic wave receiving sensitivity of the electrical noise detecting element is lowered to zero (or approximately zero) by, for example, increasing thickness of a surface of a sensor unit as compared to the acoustic wave detecting element 501. Alternatively, a similar effect of reducing acoustic wave receiving sensitivity can be created by placing a member which blocks acoustic waves on the surface of the acoustic wave detecting element 501. Furthermore, configurations of the electrical noise detecting element are not limited to the above and any configuration may be adopted as long as an effect is created to bring sensitivity with respect to acoustic waves lower than the acoustic wave detecting element 501. The electrical noise detecting element 502 configured to have an acoustic wave receiving sensitivity of zero does not output an electrical signal derived from an acoustic wave and, when electrical noise is input, the electrical noise detecting element 502 outputs an electrical signal corresponding to the input electrical noise.

In the present invention, the electrical noise detecting element 502 is also referred to as a reference element. A signal output by the reference element is also referred to as a reference signal. In addition, as will be described later, the sensitivity of the reference element with respect to acoustic waves is not limited to zero (or approximately zero) and need only differ from that of the acoustic wave detecting element. In this case, a sensitivity with respect to acoustic waves of zero (or approximately zero) means that output obtained in accordance with input of an acoustic wave is negligible. This can also be rephrased as the sensitivity with respect to acoustic waves being substantially zero.

Reference numeral 503 denotes a signal processing unit which, when receiving an instruction from the control unit 201, time-sequentially collects a plurality of electrical signals from the acoustic wave detecting element 501 and the electrical noise detecting element 502 and performs various arithmetic processing. Specifically, the signal processing unit 503 amplifies an analog electrical signal output from the acoustic wave detecting element 501 or the electrical noise detecting element 502 to a desired level and subsequently converts the amplified analog electrical signal into a digital signal. To this end, the signal processing unit 503 preferably includes an amplifier, an AD converter, a FIFO memory, and the like.

Although details will be given later, the signal processing unit 503 which is also a difference processing unit reduces a noise-derived component from an acoustic signal. In this regard, the signal processing unit 503 corresponds to a noise reducer according to the present invention. In addition, the signal processing unit 503 performs a reconstruction process using a noise-reduced signal obtained by reducing a component derived from electrical noise, and generates image data representing characteristic information of an object. In this regard, the signal processing unit 503 corresponds to a processor according to the present invention. As a configuration for realizing the image reconstruction function of the signal processing unit 503, a processing circuit or an information processing apparatus which includes a CPU and a memory and which operates in accordance with a program is preferable. Known methods such as a phasing addition method and a Fourier transform method can be adopted for image reconstruction. The signal processing unit 503 may be mounted to the same information processing apparatus as the control unit 201 or may be configured separately.

(Configuration Regarding Electrical Connection)

Figure 2A:
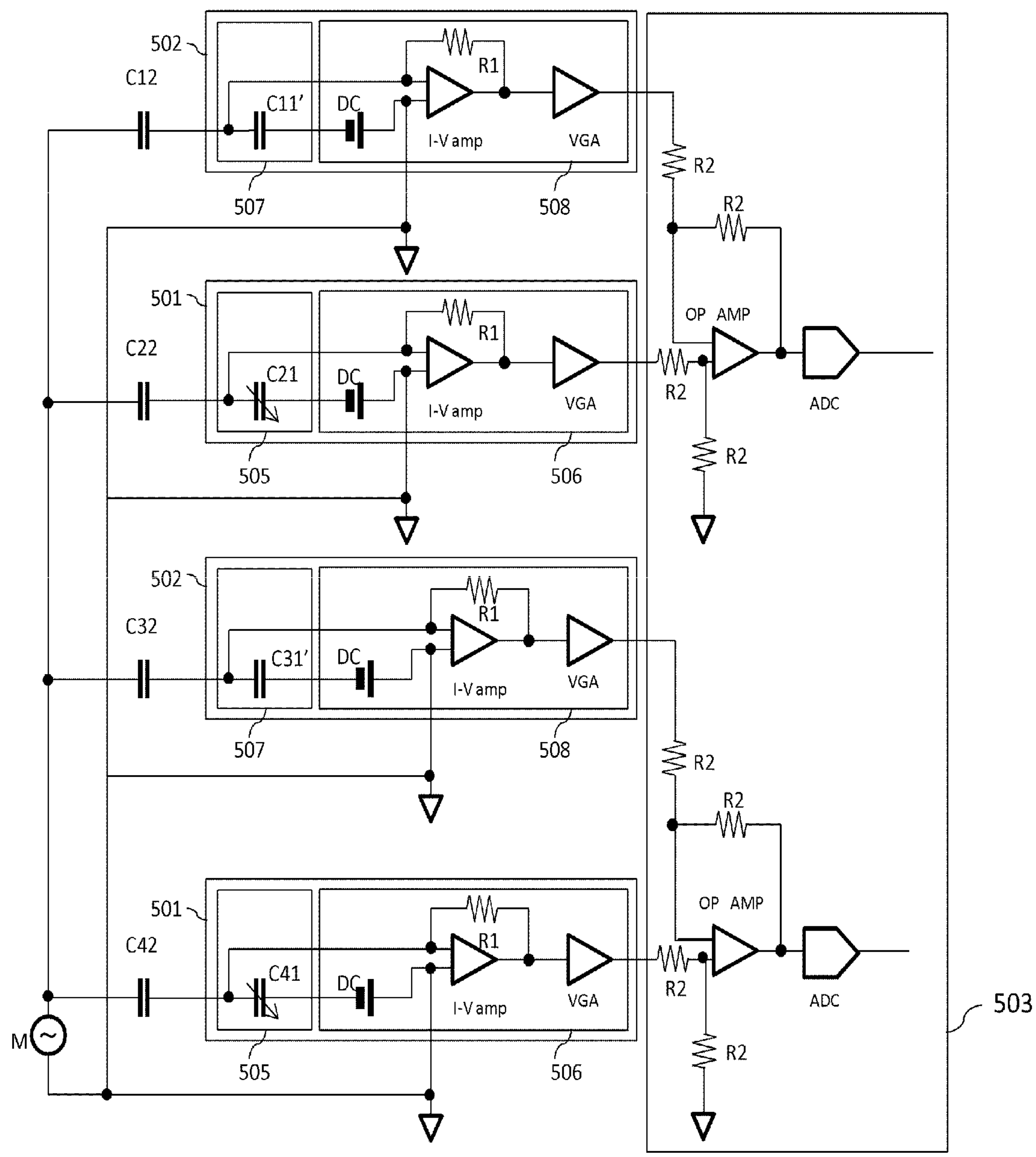
FIG. 2A is an electrical connection diagram of an acoustic wave detecting element group and an electrical noise detecting element group according to the first embodiment.

Next, an electrical connection of an acoustic wave detecting element group and an electrical noise detecting element group according to the first embodiment of the present invention will be described using FIG. 2A. The acoustic wave detecting element 501, the electrical noise detecting element 502, and the signal processing unit 503 have already been described above.

Reference numeral 505 denotes an acoustic wave detecting unit. Specifically, in the case of a CMUT, a configuration is adopted in which a change in capacitance that occurs upon receiving an acoustic wave is detected as an electrical signal and, in the case of a piezoelectric element, a configuration is adopted in which a change in electromotive force that occurs upon receiving an acoustic wave is detected as an electrical signal. In this case, the description will proceed on the assumption of a CMUT.

Reference numeral 506 denotes an acoustic signal amplifying unit which amplifies an electrical signal obtained by the acoustic wave detecting unit 505. Specifically, the acoustic signal amplifying unit 506 is constituted by a current-voltage converter which converts a change in an amount of electric charge (in other words, a current) accompanying a change in capacity of the CMUT into a voltage, and an amplifier.

Reference numeral 507 denotes an electrical noise detecting unit. Specifically, acoustic wave receiving sensitivity of the acoustic wave detecting unit 505 is lowered to zero (or approximately zero). An example of a configuration for lowering acoustic wave receiving sensitivity to zero is a method of using a heavy material or a hard material in a portion which comes into contact with the acoustic matching liquid 205 of a surface of the acoustic wave detecting unit 505. Alternatively, there is a method of adopting a configuration similar to the acoustic wave detecting unit 505 but installing the configuration so as not to come into contact with the acoustic matching liquid 205.

Reference numeral 508 denotes an electrical noise amplifying unit which has similar electrical characteristics to the acoustic signal amplifying unit 506. Specifically, the electrical noise amplifying unit is constituted by a current-voltage converter which converts a change in an amount of electric charge (in other words, a current) accompanying a change in capacity of the CMUT into a voltage, and an amplifier.

Reference character "M" denotes a noise source and is shown as a voltage source in an equivalent circuit for the sake of description. Specific examples of a noise generation source include the motor included in the supporter driving unit 208, a linear scale for detecting a position during driving, and a peripheral circuit such as a switching power supply. "I-Vamp" denotes a current-voltage conversion circuit for converting a current of an acoustic signal or a current of electrical noise into voltage.

Reference character R1 denotes a feedback resistor of a current-voltage converter, and reference character R2 denotes a resistor for determining a gain of a differential amplifier. "VGA" denotes a variable gain amplifier for amplifying an acoustic signal or electrical noise. Moreover, gains of all variable gain amplifiers VGA are set to a same gain. "OP AMP" denotes an operational amplifier for acquiring a differential signal of an acoustic signal and electrical noise. "ADC" denotes an AD converter for converting a differential signal of an acoustic signal and electrical noise into a digital value. Output of the ADC is used to reconstruct an image in the signal processing unit 503. "DC" denotes a direct-current power supply for applying a bias voltage of a CMUT.

C21 and C41 denote acoustic wave detecting element capacitors included in the acoustic wave detecting unit 505. When an acoustic wave reaches the acoustic wave detecting unit 505, due to a change in a distance between electrodes of the acoustic wave detecting element capacitors C21 and C41 in accordance with sound pressure, amounts of electric charge of the acoustic wave detecting element capacitors C21 and C41 change. The change in the amounts of electric charge (in other words, currents) of the acoustic wave detecting element capacitors C21 and C41 is converted into voltage by I-Vamp, and voltage based on the acoustic wave is generated in output to the acoustic signal amplifying unit 506.

C11' and C31' denote electrical noise detecting element capacitors included in the electrical noise detecting unit 507. Since acoustic waves do not reach the electrical noise detecting unit 507, a distance between electrodes of the electrical noise detecting element capacitors C11' and C31' is unchanged. When there is no electrical noise, output voltage to the electrical noise amplifying unit 508 is constant.

C12, C22, C32, and C42 denote capacitors between the acoustic wave detecting element 501 and the electrical noise detecting element 502 with respect to a power supply M when noise of a motor is modeled by a voltage source M. By setting a physical distance between the acoustic wave detecting element 501 and the electrical noise detecting element 502 shorter than a distance between the motor and the acoustic wave detecting element 501 and the distance between the motor and the electrical noise detecting element 502, relationships of approximately C12=C22 and C32=C42 can be established. As a result, output voltage attributable to noise can be made approximately the same between the acoustic wave detecting element 501 and the electrical noise detecting element 502. Noise of a noise source M is transmitted to I-Vamp input terminals of the acoustic wave detecting element 501 and the electrical noise detecting element 502 via capacitors as shown in FIG. 2A.

In the present embodiment, at the signal processing unit 503, a differential signal of the acoustic wave detecting element 501 and the electrical noise detecting element 502 is acquired using a differential amplification circuit constituted by an operational amplifier (OP AMP). Accordingly, electrical noise included in an acoustic signal of the acoustic wave detecting element 501 can be acquired. By subtracting the electrical noise from the acoustic signal, a component derived from noise can be removed or reduced.

In the present embodiment, the acoustic wave detecting elements 501 and the electrical noise detecting elements 502 are associated with each other on a one-to-one basis. Such a configuration is adopted because, depending on a distance from the motor or a transmission route of electrical noise, a difference arises in phases or amplitudes of electrical noise superimposed on the acoustic signals of the respective acoustic wave detecting elements 501. However, the one-to-one correspondence of the acoustic wave detecting elements 501 and the electrical noise detecting elements 502 is not essential. For example, in accordance with a distance from a noise source, one electrical noise detecting element 502 may be provided in a region in which capacitances between the acoustic wave detecting elements 501 and the electrical noise detecting elements 502 with respect to the power supply M are approximately equal. The configuration in this case determines a difference from one electrical noise detecting element 502 with respect to a plurality of acoustic wave detecting elements 501 to which input of approximately equal noise is assumed. In order to bring effects of electrical noise input to the acoustic wave detecting elements 501 and the electrical noise detecting elements 502 close to each other, the acoustic wave detecting elements 501 and the electrical noise detecting elements 502 are favorably provided in proximity to each other.

(Flow of Processing)

Figure 3:
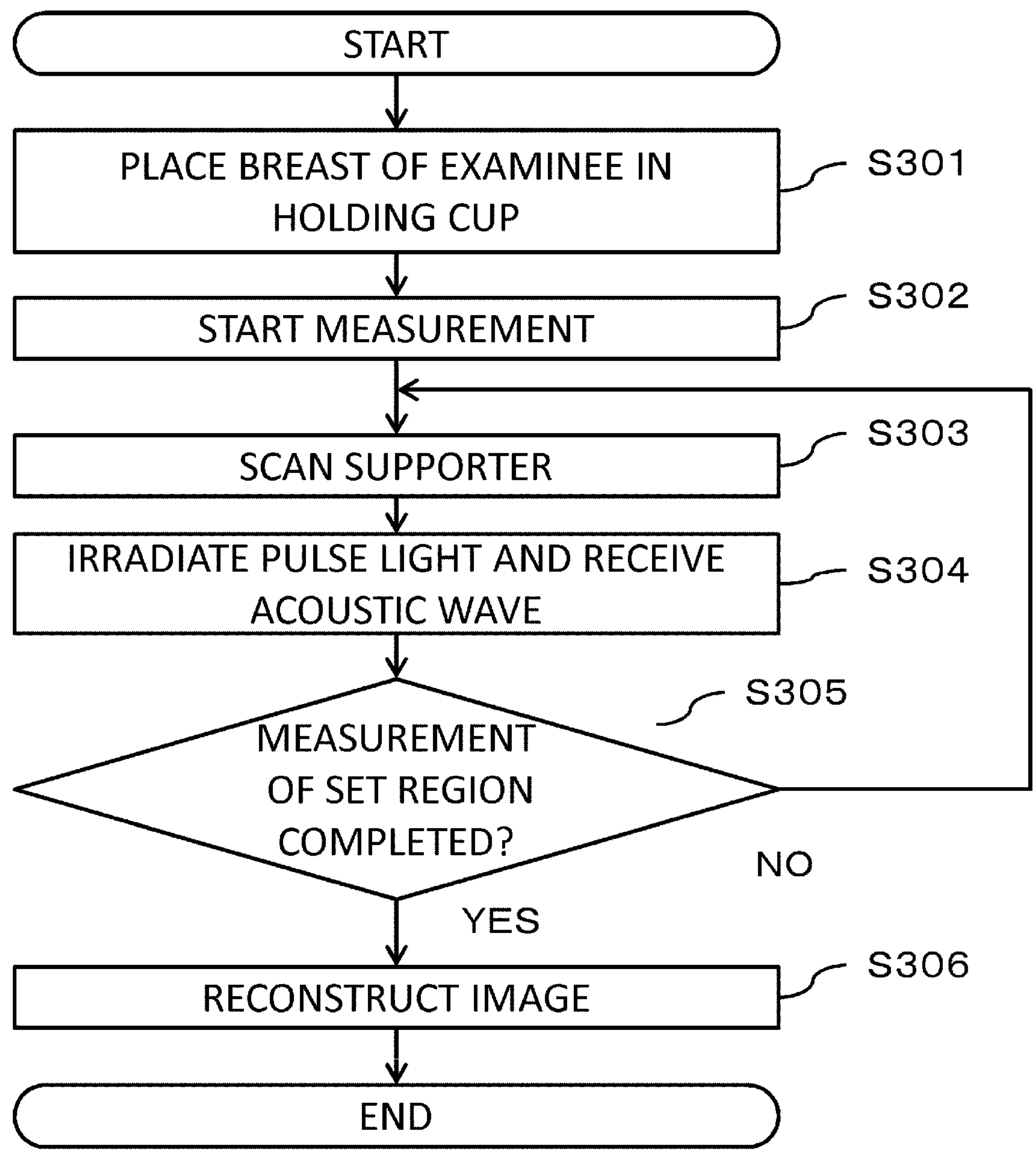
FIG. 3 shows a measurement sequence according to the first embodiment.

A measurement sequence according to the first embodiment of the present invention will be explained below with reference to FIG. 3. In step S301, the examinee 100 is asked to lie face down and insert the object section 101 (in this case, abreast is assumed) into a holding cup. Next, the sequence proceeds to step S302 to start measurement.

In step S303, control of a scanning range is performed. In step S304, pulsed light is irradiated from the light irradiating unit 403. Moreover, depending on a scanning pattern, S303 and S304 are practically integrally executed. The acoustic wave detecting element 501 receives an acoustic wave excited by a light absorber inside the object section 101 due to irradiated pulsed light and outputs an electrical signal including a component desired from the acoustic wave. The electrical signal also includes a component derived from electrical noise. In parallel with the output of the electrical signal from the acoustic wave detecting element 501, the electrical noise detecting element 502 outputs a reference signal in accordance with the electrical noise. Due to processing in the signal processing unit 503, a differential signal of both signals is output, digitized, and stored in a memory.

In step S305, a check is performed on whether or not the scan has been completed. Specifically, a check is performed on whether or not an entire scan range set in advance has been measured. When the scan has been completed (YES in S305), the measurement is ended.

In step S306, the signal processing unit 503 performs an imaging process such as image reconstruction using the differential signal to acquire image data representing a distribution of characteristic information in the object. Since the differential signal is a signal after noise reduction obtained by subtracting a reference signal from an acoustic signal, an image based on the generated image data is a preferable image in which a component derived from noise has been reduced.

(Modification)

Figure 2B:
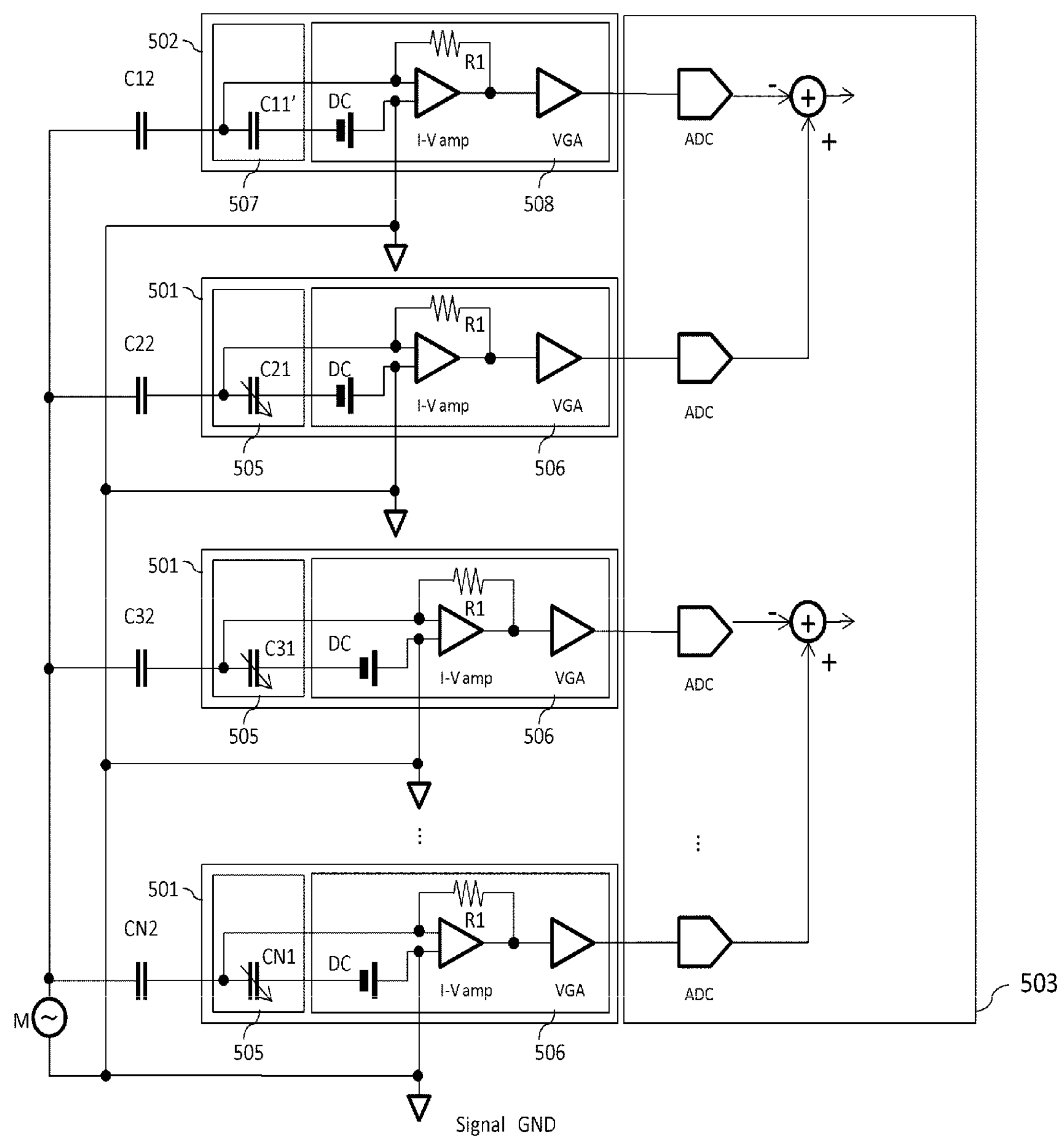
FIG. 2B is another electrical connection diagram of an acoustic wave detecting element group and an electrical noise detecting element group according to the first embodiment.

Moreover, a subtraction process by an analog circuit has been described with reference to FIG. 2A. Alternatively, as shown in FIG. 2B, outputs of each acoustic wave detecting element 501 and each electrical noise detecting element 502 may be respectively independently converted into a digital value by the ADC. Even in this case, a component derived from noise is reduced by a subtraction process in which a reference signal is subtracted from an acoustic signal. Subsequently, preferable image data is obtained by image reconstruction using a noise-reduced signal. In addition, in this case, an acoustic signal and a reference signal may be individually stored in a memory and an image based on the acoustic signal and an image based on the reference signal may be respectively generated. Image data in which a component derived from noise is reduced can also be obtained by a method of subtracting the image based on the reference signal from the image based on the acoustic signal.

As described above, according to the first embodiment of the present invention, electrical noise from a motor which is superimposed on an acoustic signal of each acoustic wave detecting element 501 via a capacitor can be individually detected. In addition, by subtracting a noise component from an acoustic signal, a preferable reconstructed image can be acquired.

In the description provided above, CMUT are used as the acoustic wave detecting unit 505 and the electrical noise detecting unit 507. However, similar effects are produced with a configuration using piezoelectric elements. In this case, the I-Vamp is no longer necessary and the piezoelectric elements may be directly connected to a variable gain amplifier (VGA). When output voltage of the piezoelectric elements is insufficient, a preamplifier (not shown) may be provided as necessary between the piezoelectric elements and the variable gain amplifier VGA.

<Second Embodiment>

Next, an electrical connection of the acoustic wave detecting element 501 group and the electrical noise detecting element 502 according to a second embodiment will be described using FIG. 4. Since the respective reference characters are similar to those shown in FIG. 2, a description thereof will be omitted.

An apparatus according to the present embodiment is configured to include one electrical noise detecting element 502 with respect to an acoustic wave detecting element group constituted by a plurality of acoustic wave detecting elements 501. Such a configuration is adopted because there are cases where, depending on a distance from a noise source such as a motor to an element or on a noise transmission route from the noise source, phases or amplitudes of electrical noise superimposed on acoustic signals are almost the same among the plurality of acoustic wave detecting elements 501. For example, when a physical distance between the acoustic wave detecting element 501 and the electrical noise detecting element 502 is shorter than a distance between the noise source and the acoustic wave detecting element 501 and the distance between the noise source and the electrical noise detecting element 502, a relationship of approximately C12=C22=C32=C42 is established.

Moreover, the number of the electrical noise detecting element 502 corresponding to the acoustic wave detecting element group is not limited to one. For example, the electrical noise detecting element 502 may be provided in plurality, and an average value of reference signals (electrical noise average value) may be obtained and applied to each acoustic wave detecting element 501 included in the acoustic wave detecting element group. In addition, the number of acoustic wave detecting elements 501 included in one acoustic wave detecting element group is not limited as long as the conditions described above are satisfied.

Figure 4A:
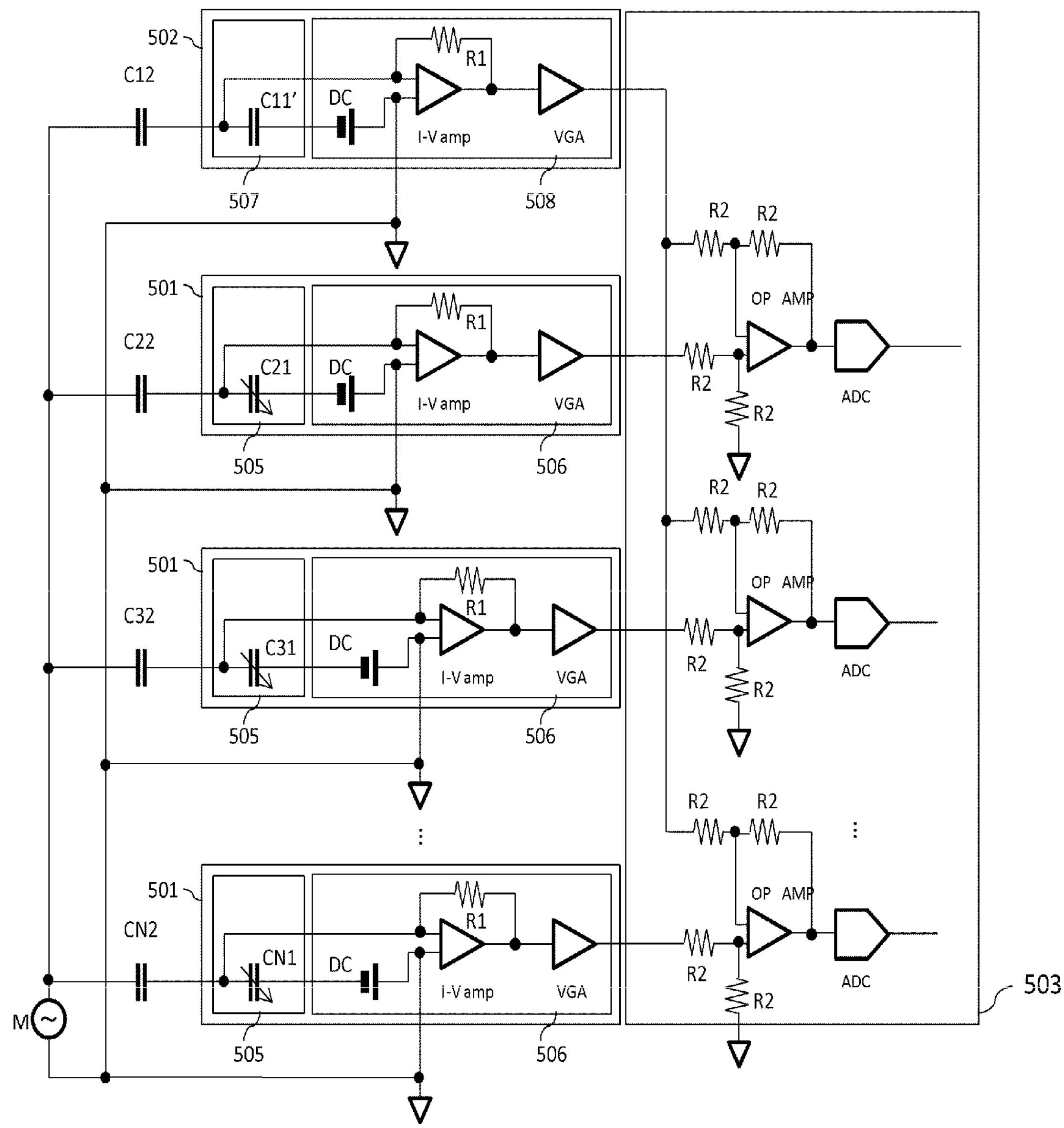
FIG. 4A is an electrical connection diagram of an acoustic wave detecting element group and an electrical noise detecting element group according to a second embodiment.
Figure 4B:
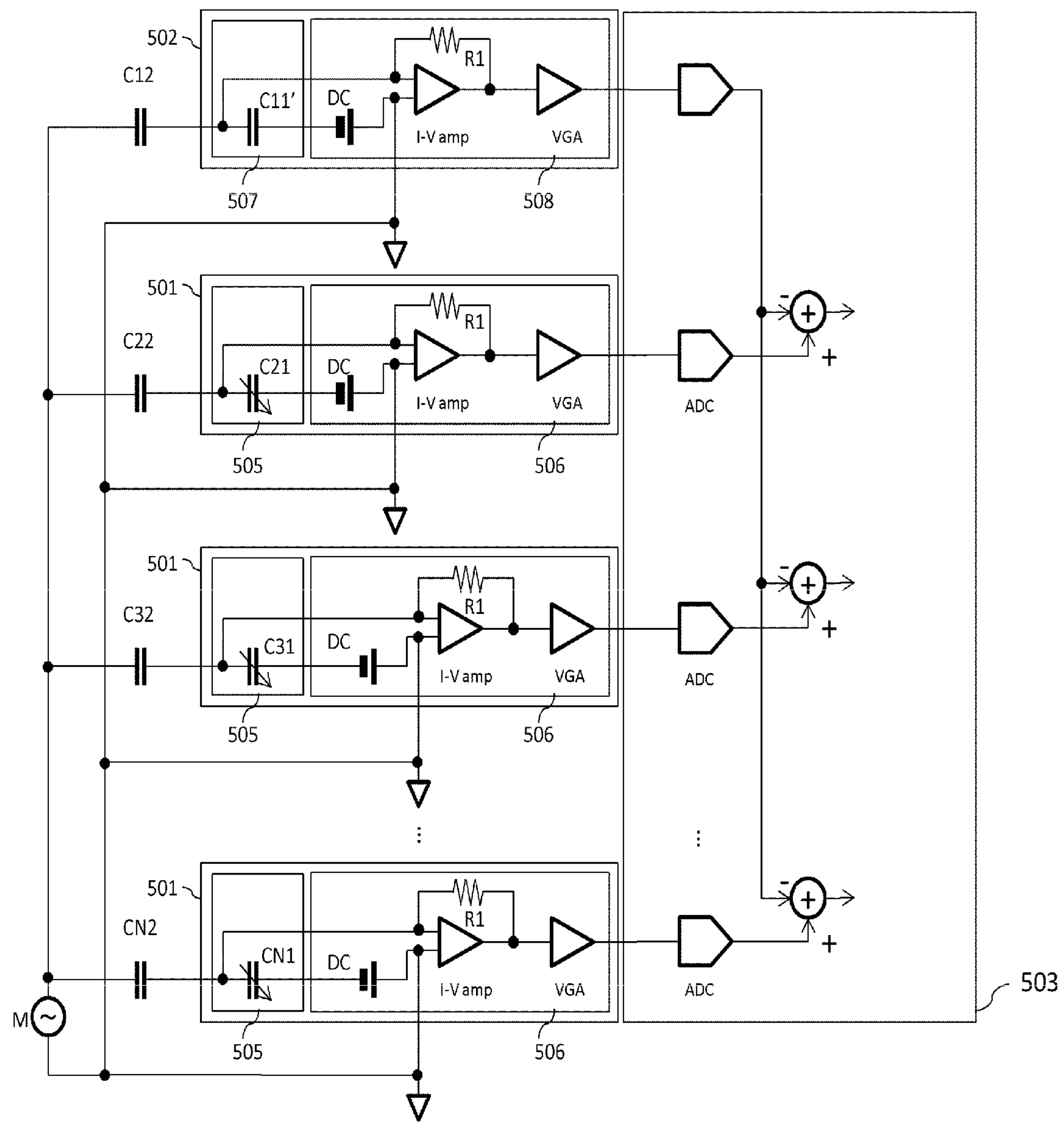
FIG. 4B is another electrical connection diagram of an acoustic wave detecting element group and an electrical noise detecting element group according to the second embodiment.

Moreover, in the configuration shown in FIG. 4A, a subtraction process is performed by an analog circuit. Alternatively, as shown in FIG. 4B, a subtraction process may be performed after converting outputs of each acoustic wave detecting element 501 and each electrical noise detecting element 502 into a digital value by an ADC. When this configuration is adopted, since a same value is uniformly subtracted from outputs of all acoustic wave detecting elements 501, a simpler circuit configuration than that realized by an analog circuit can be obtained.

According to the second embodiment, when phases or amplitudes of electrical noise superimposed on outputs of the acoustic wave detecting elements 501 are equal, electrical noise from a motor that is superimposed on acoustic signals of the respective acoustic wave detecting elements 501 can be collectively subtracted from the outputs of the acoustic wave detecting elements 501. In addition, a preferable reconstructed image can be generated by a simple configuration having a small number of electrical noise detecting elements 502.

<Third Embodiment>

Figure 5:
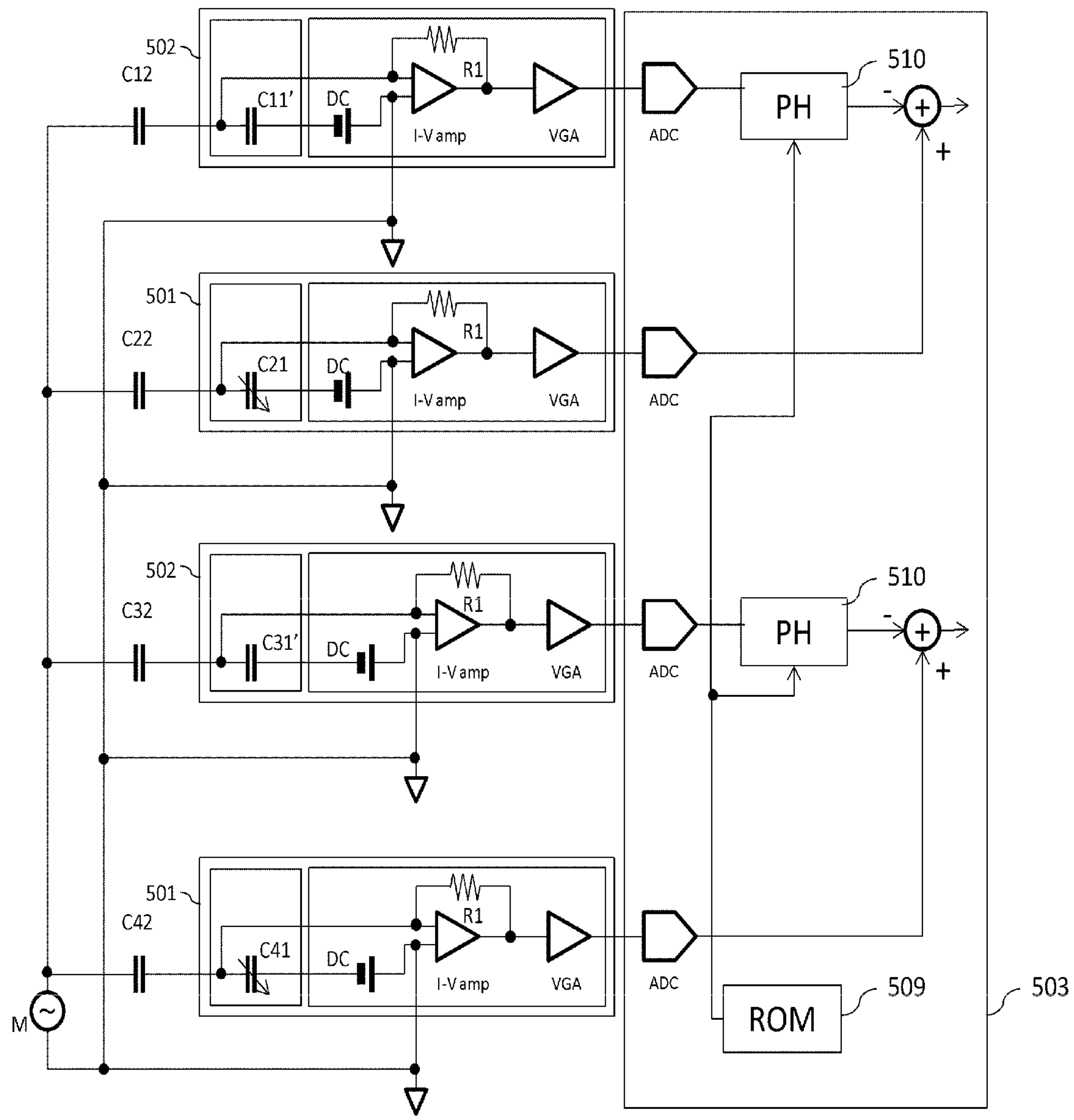
FIG. 5 is an electrical connection diagram of an acoustic wave detecting element group and an electrical noise detecting element group according to a third embodiment.

Next, an electrical connection of the acoustic wave detecting element 501 group and the electrical noise detecting element 502 group according to a third embodiment will be described using FIG. 5. Moreover, a description of same reference characters as FIG. 2 will be omitted.

(Configuration Regarding Electrical Connection)

The third embodiment includes an electrical noise detecting element 502 corresponding to each acoustic wave detecting element 501 in a similar manner to the first embodiment. Such a one-to-one correspondence of the acoustic wave detecting elements 501 and the electrical noise detecting elements 502 is adopted because differences in a distance or a noise transmission route from a noise source such as a motor to each element results in differences in phases or amplitudes of electrical noise superimposed on acoustic signals. For example, by making a physical distance between the acoustic wave detecting element 501 and the electrical noise detecting element 502 shorter than a distance between the noise source and the acoustic wave detecting element 501 and the distance between the noise source and the electrical noise detecting element 502, relationships of approximately C12=C22 and C32=C42 are established.

However, the one-to-one correspondence of the numbers of acoustic wave detecting elements 501 and the electrical noise detecting elements 502 in the apparatus is not essential. For example, a configuration may be adopted in which an installation area of acoustic wave detecting elements 501 in the apparatus is divided into a plurality of areas and one electrical noise detecting element 502 is provided in each divided area. In this case, with respect to a plurality of acoustic wave detecting elements 501 in a same area, a reference signal from the electrical noise detecting element 502 for the area is applied.

Reference numeral 509 denotes a ROM (recording unit) which records an electrical noise signal of the electrical noise detecting element 502 acquired in advance. Using the ROM as a recording unit provides an advantage in that information can be stored even when power to the apparatus is shut down. Electrical noise is measured in advance in a state where the examinee 100 is absent. In addition, random noise may be removed by performing a plurality of measurements in advance and recording an average value while matching phases of electrical noise. Removing random noise from electrical noise prevents a random noise component in a signal after subtraction from increasing.

Reference numeral 510 denotes a subtraction signal generating unit. The subtraction signal generating unit 510 compares a phase of electrical noise stored in the ROM 509 and a phase of an output of the electrical noise detecting element 502 with each other, and generates a subtraction signal by adjusting the phase of the electrical noise stored in the ROM 509 so as to conform to the phase and amplitude of the output of the electrical noise detecting element 502. Electrical noise is reduced as a subtraction circuit subtracts a corresponding output of the subtraction signal generating unit 510 from an output of each acoustic wave detecting element 501.

(Flow of Processing)

Figure 6:
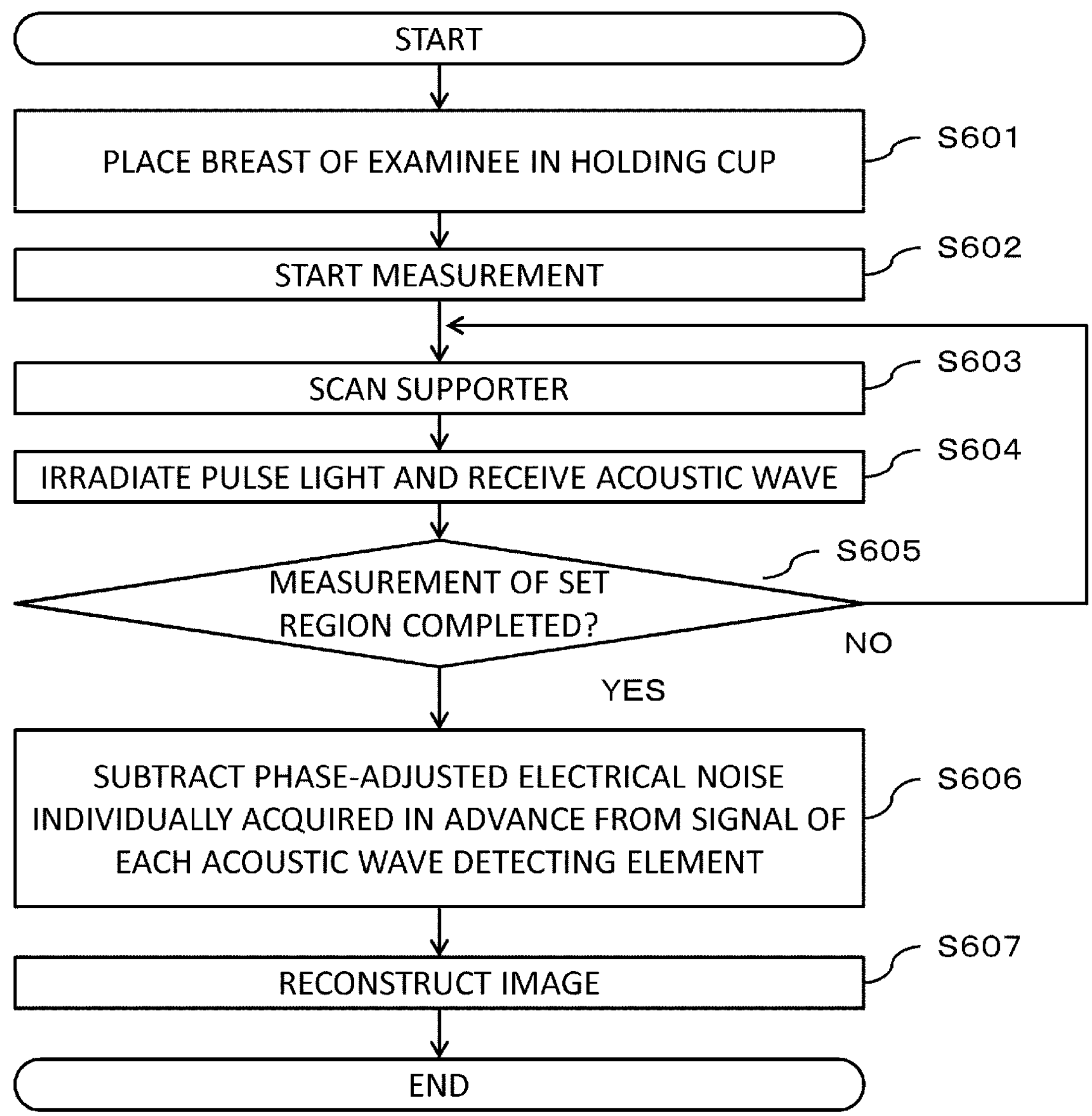
FIG. 6 shows a measurement sequence according to the third embodiment.

A measurement sequence according to the third embodiment will now be described with reference to FIG. 6. Contents of processing of steps S601 to S605 correspond to those of S301 to S305 in FIG. 3. When scanning has been completed (YES in S605), in step S606, the subtraction signal generating unit 510 adjusts a phase and an amplitude of an electrical noise signal stored in the ROM 509 based on a signal of the electrical noise detecting element 502. Subsequently, the generated electrical noise is subtracted from an acoustic signal. In step S607, the signal processing unit 503 performs image reconstruction and generates image data.

According to the third embodiment, a phase and an amplitude of electrical noise acquired in advance are adjusted in association with a phase and an amplitude of electrical noise to be superimposed on each acoustic wave detecting element 501. By obtaining an acoustic signal by individually subtracting electrical noise obtained as described above from an output of each acoustic wave detecting element 501, a preferable reconstructed image can be acquired while suppressing an increase in random noise.

<Fourth Embodiment>

Figure 7:
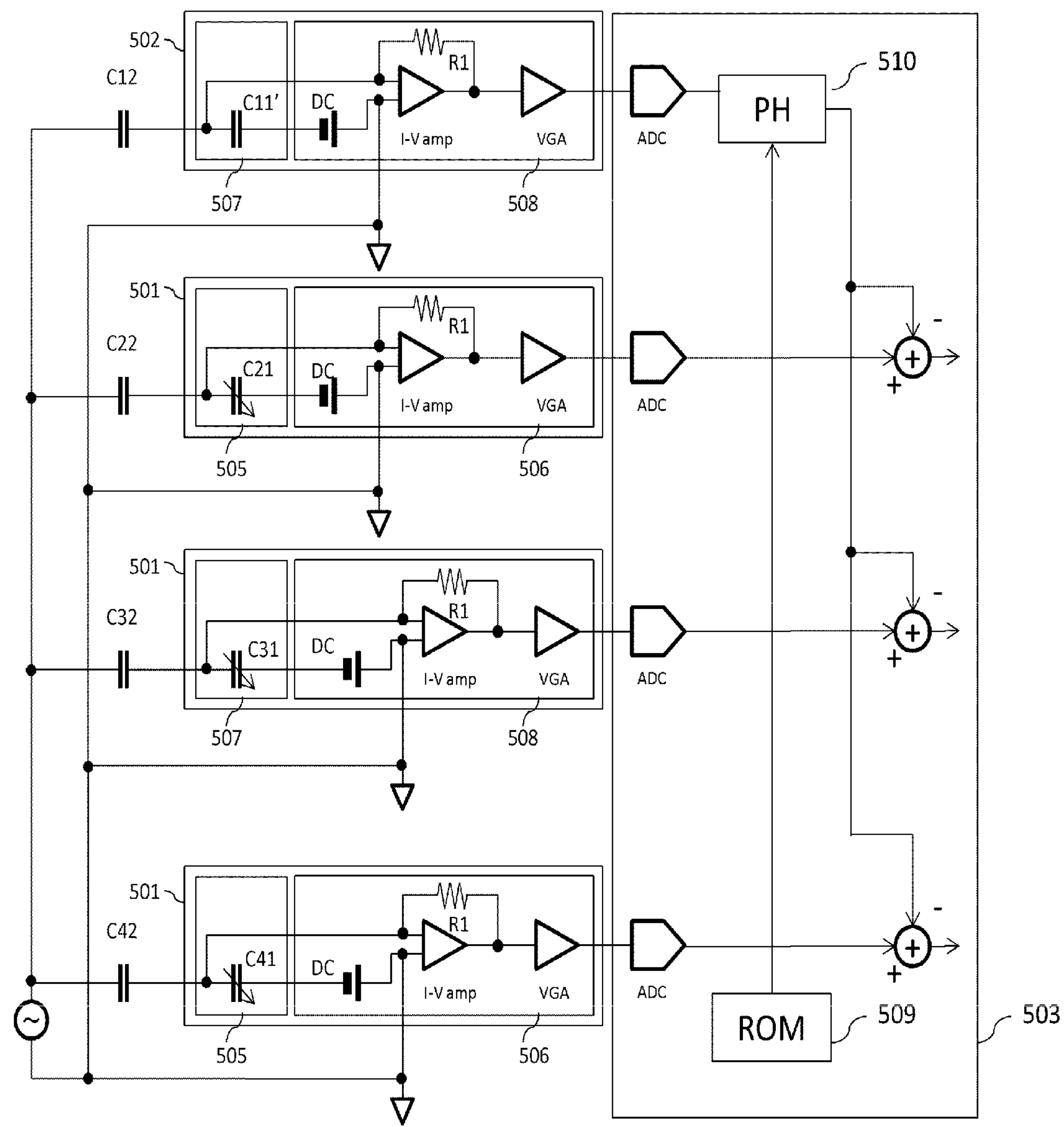
FIG. 7 is an electrical connection diagram of an acoustic wave detecting element group and an electrical noise detecting element group according to a fourth embodiment.

Next, an electrical connection of the acoustic wave detecting element 501 group and the electrical noise detecting element 502 according to a fourth embodiment will be described using FIG. 7. Moreover, a description of same reference characters as FIG. 5 will be omitted.

(Configuration Regarding Electrical Connection)

The fourth embodiment characteristically adopts a configuration in which only one electrical noise detecting element 502 is included with respect to a plurality of acoustic wave detecting elements 501. Such a configuration is adopted because, in a similar manner to the second embodiment, depending on a distance or a noise transmission route from a noise source such as a motor to an element, phases or amplitudes of electrical noise superimposed on acoustic signals of the respective acoustic wave detecting elements 501 are the same (almost the same).

In addition, in the fourth embodiment, only one subtraction signal generating unit 510 is included in the signal processing unit 503. Furthermore, electrical noise is stored in the ROM 509 in advance. The subtraction signal generating unit 510 compares a phase of the stored electrical noise and a phase of an output of the electrical noise detecting element 502 with each other, and generates a subtraction signal by adjusting the phase and the amplitude of the electrical noise stored in the ROM 509 so as to conform to the output of the electrical noise detecting element 502. In addition, a subtraction circuit performs a subtraction process using an output of the subtraction signal generating unit 510 with respect to outputs of all acoustic wave detecting elements 501. Accordingly, electrical noise can be reduced.

(Flow of Processing)

A measurement sequence according to the fourth embodiment of the present invention will be explained below. An outline of the sequence is similar to that shown in FIG. 6. In addition, in a noise subtraction process in step S606, phases of signals of all acoustic wave detecting elements 501 are adjusted based on a signal of the electrical noise detecting element 502 acquired in advance and stored in the ROM 509, and electrical noise is subtracted from the signals of all acoustic wave detecting elements 501. Reconstruction can be executed in a similar manner to the respective embodiments described above.

According to the fourth embodiment, when phases or amplitudes of electrical noise superimposed on acoustic signals of the respective acoustic wave detecting elements 501 via capacitors are approximately equal among the elements, acoustic signals can be acquired by collectively performing a subtraction process using electrical noise acquired in advance. As a result, a preferable reconstructed image can be generated while suppressing an increase in random noise during subtraction by a simple configuration having a small number of electrical noise detecting elements 502.

<Fifth Embodiment>

Next, an electrical connection of the acoustic wave detecting element 501 group and the electrical noise detecting element 502 according to a fifth embodiment will be described using FIG. 8.

(Configuration Regarding Electrical Connection)

Figure 8:
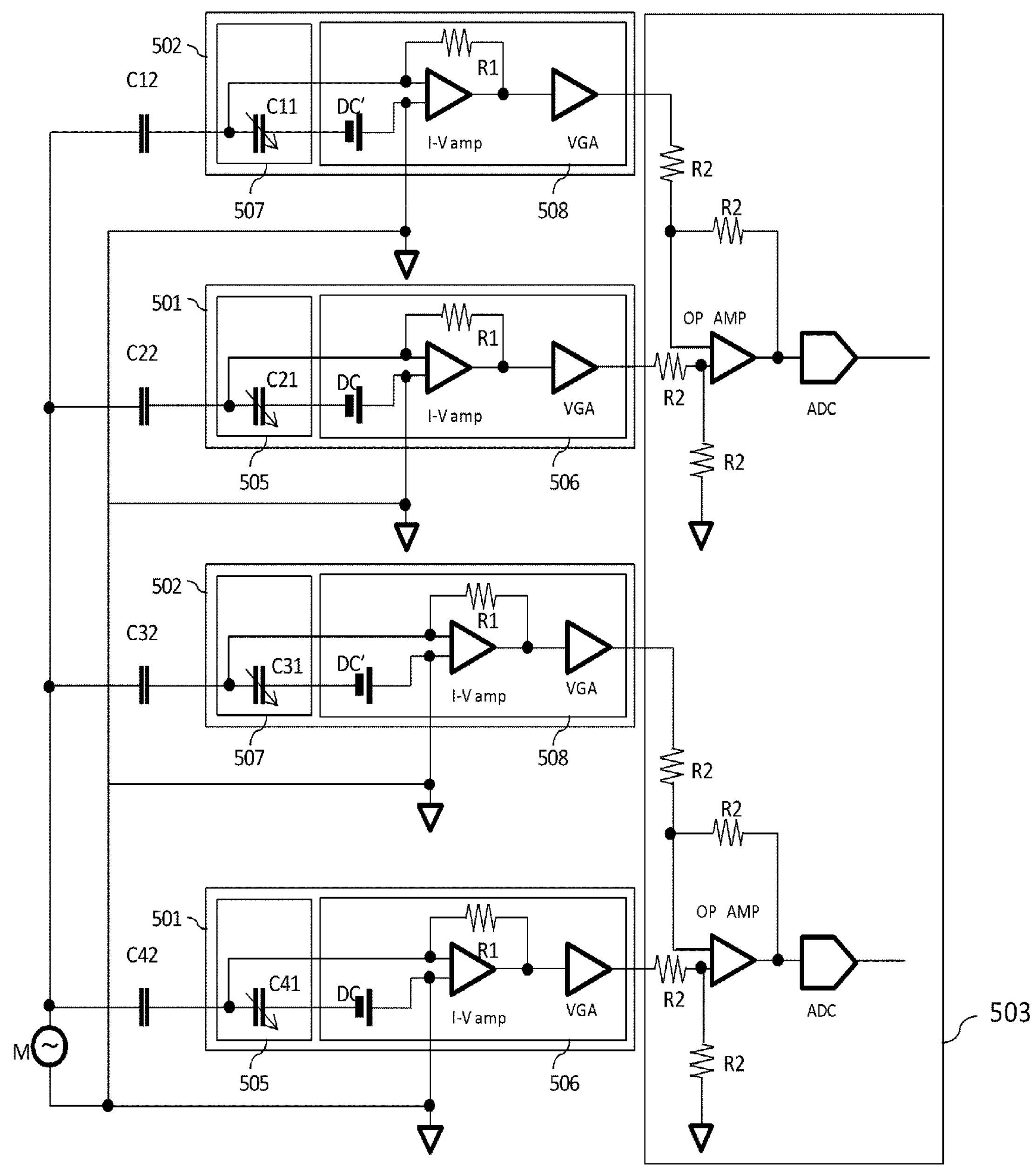
FIG. 8 is an electrical connection diagram of an acoustic wave detecting element group and an electrical noise detecting element group according to a fifth embodiment.
Figure 9A:
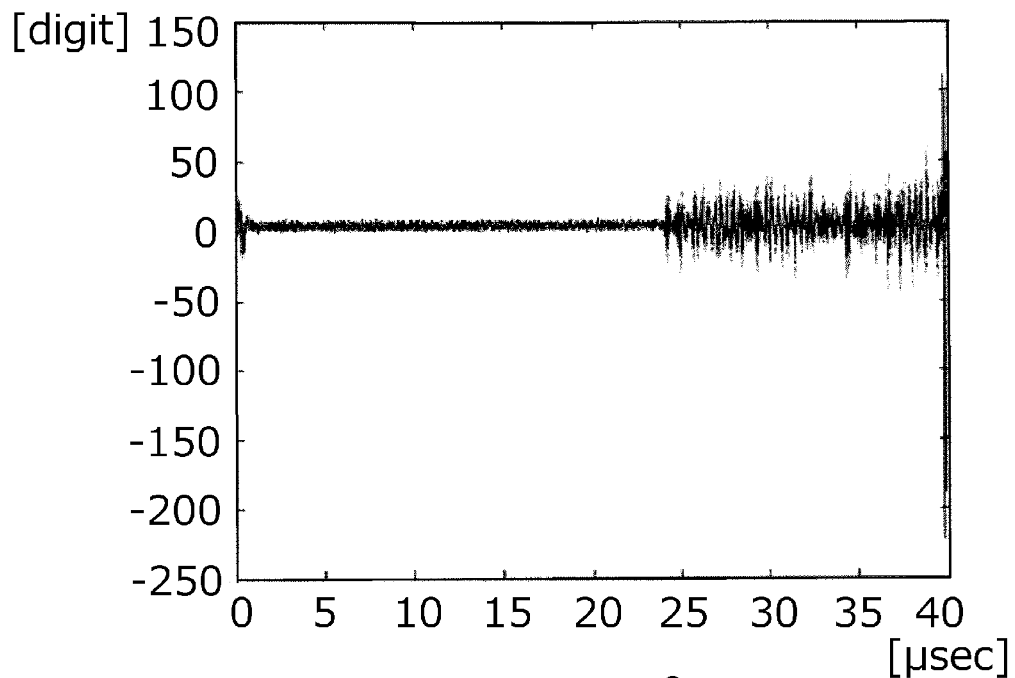
FIGS. 9A and 9B are diagrams showing related art.
Figure 9B:
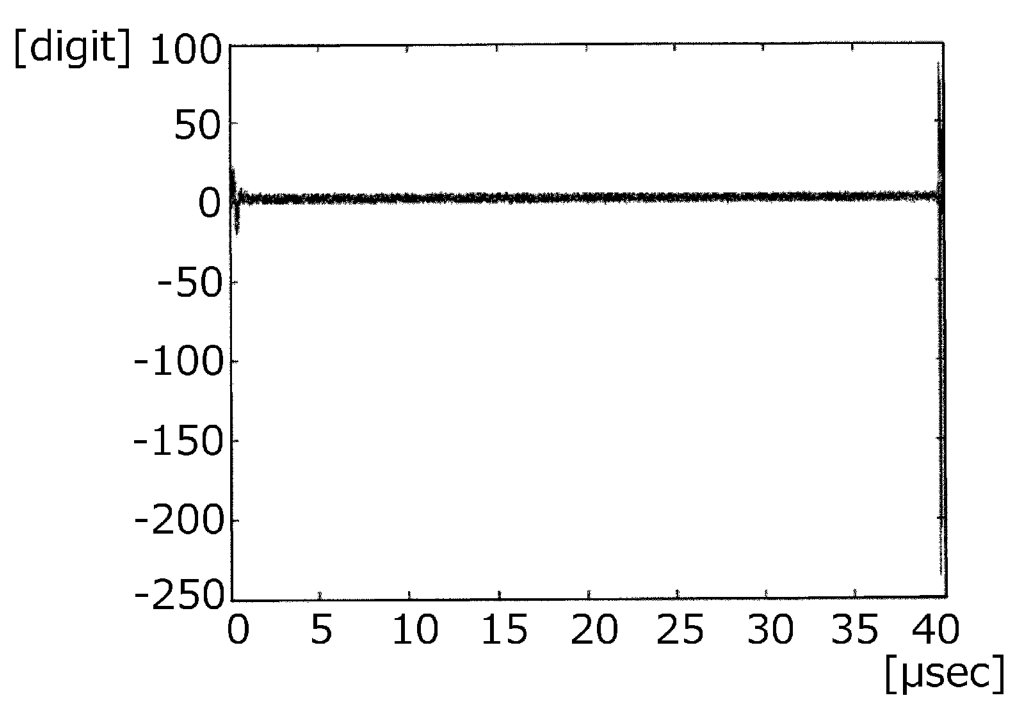

A feature of an apparatus shown in FIG. 8 is that the electrical noise detecting unit 507 in the electrical noise detecting element 502 also has sensitivity with respect to acoustic waves. A description of same reference characters as FIG. 2 will be omitted.

Reference characters C11 and C31 denote electrical noise/acoustic wave detecting element capacitors which detect electrical noise and acoustic waves in the electrical noise detecting unit 507. Sound pressure receiving sensitivity of the electrical noise/acoustic wave detecting element capacitors C11 and C31 is characteristically lower than that of acoustic wave detecting element capacitors C21 and C41. In order to lower sensitivity, for example, there is a method of varying voltage of a direct-current power supply DC for applying bias voltage of CMUT between the acoustic wave detecting element 501 and the electrical noise detecting element 502. By setting a bias voltage DC' of the CMUT for electrical noise detection lower than a bias voltage DC of other CMUT, a difference in voltage between electrodes sandwiching the respective capacitors of the electrical noise/acoustic wave detecting element capacitors C11 and C31 decreases. As a result, since a distance between the electrodes expands and capacitance increases, receiving sensitivity of acoustic waves declines.

Such a configuration is adopted because, when acoustic wave receiving sensitivity of the electrical noise detecting element 502 is lower than acoustic wave receiving sensitivity of the acoustic wave detecting element 501, electrical noise can be reduced by obtaining a differential signal between both acoustic wave receiving sensitivities. Accordingly, an SN ratio can be improved and a preferable reconstructed image can be acquired. In other words, by obtaining a difference between a pair of electrical signals output from a pair of acoustic wave detecting elements with mutually different sensitivities with respect to acoustic waves, a signal can be obtained in which a component derived from electrical noise that is commonly superimposed on both electrical signals has been reduced. It is expected that a preferable image can be obtained by performing image reconstruction using such signals.

In addition, by setting the acoustic wave receiving sensitivity of the electrical noise detecting element 502 low enough so as to be negligible with respect to the acoustic wave receiving sensitivity of the acoustic wave detecting element 501, a maximum SN ratio similar to that of the first embodiment may be obtained. Furthermore, the fourth embodiment can be executed by a similar measurement sequence to the first embodiment.

Moreover, a subtraction process by an analog circuit has been described with reference to FIG. 10. Alternatively, in a similar manner to the first embodiment, a subtraction process may be performed after converting outputs of each acoustic wave detecting element 501 and each electrical noise detecting element 502 into a digital value by an ADC. In addition, noise may be reduced by obtaining a difference in generated image data.

As described above, according to the fifth embodiment of the present invention, electrical noise superimposed on an output of the acoustic wave detecting element 501 is subtracted from an output of the electrical noise detecting element 502 to which is applied a bias voltage DC' of a CMUT that is lower than a bias voltage DC of the CMUT. According to this configuration, a shielding structure for preventing the electrical noise detecting element 502 from detecting an acoustic wave such as the use of a heavy material or a hard material on a surface of the acoustic wave detecting unit 505 which comes into contact with the acoustic matching liquid 205 or installing the configuration so that the acoustic wave detecting unit 505 does not to come into contact with the acoustic matching liquid 205 is no longer necessary. As a result, a preferable reconstructed image can be acquired by a simple configuration of merely changing bias voltages to be applied to the acoustic wave detecting element 501 and the electrical noise detecting element 502.

In addition, the configurations according to the first to fourth embodiments can be considered cases where sensitivity of one of a pair of acoustic wave detecting elements according to the present embodiment with respect to acoustic waves is substantially zero.

(Other Embodiments)

While a motor for moving an acoustic wave detecting element relative to an object, a linear scale, a switching power supply, or the like has been explained as an electrical noise source in the description presented above, configurations according to the respective embodiments of the present invention are also effective with respect to electrical noise input from electrical noise sources other than those described above.

The present invention can also be achieved by supplying a program that realizes one or more functions of the embodiments described above to a system or an apparatus via a network or a storage medium and having one or more processors in a computer in the system or the apparatus read and execute the program. Alternatively, the present invention can also be achieved by a circuit (for example, an ASIC) which realizes one or more functions.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-250981, filed on Dec. 24, 2015, which is hereby incorporated by reference herein in its entirety.

What is claimed is:

1. An object information acquiring apparatus comprising:

an acoustic wave detecting element which detects an acoustic wave propagating from an object and which outputs an acoustic signal;

a reference element having a lower sensitivity with respect to the acoustic wave than the acoustic wave detecting element, the reference element receiving an electrical noise corresponding to electrical noise input to the acoustic wave detecting element and the reference element outputting a reference signal;

a noise reducer which reduces a component derived from the electrical noise by subtracting the reference signal from the acoustic signal; and a processor which generates image data representing characteristic information of the object using the acoustic signal in which the component derived from the electrical noise has been reduced.

2. The object information acquiring apparatus according to claim 1, wherein the reference element is obtained by increasing thickness of a surface thereof as compared to the acoustic wave detecting element or by installing a member which shields the acoustic wave on the surface.

3. The object information acquiring apparatus according to claim 1, wherein the acoustic wave detecting element and the reference element are constituted by CMUT.

4. The object information acquiring apparatus according to claim 3, wherein a bias voltage applied to the reference element is lower than a bias voltage applied to the acoustic wave detecting element.

5. The object information acquiring apparatus according to claim 1, further comprising a supporter which supports the acoustic wave detecting element and the reference element.

6. The object information acquiring apparatus according to claim 5, wherein the supporter supports an acoustic matching liquid, and the electrical noise is input to the acoustic wave detecting element via the acoustic matching liquid.

7. The object information acquiring apparatus according to claim 5, further comprising a mover which moves the supporter relative to the object.

8. The object information acquiring apparatus according to claim 7, wherein the electrical noise is derived from a motor of the mover or from a switching power supply of the object information acquiring apparatus.

9. The object information acquiring apparatus according to claim 1, wherein the acoustic wave detecting element and the reference element correspond to each other one to one.

10. The object information acquiring apparatus according to claim 1, comprising a plurality of the acoustic wave detecting elements, wherein one reference element is provided for a group of acoustic wave detecting elements to which approximately equal electrical noise is input among the plurality of acoustic wave detecting elements.

11. The object information acquiring apparatus according to claim 1, comprising a plurality of the acoustic wave detecting elements and a plurality of the reference elements, wherein an average value of a plurality of reference signals output from the plurality of reference elements is applied to a plurality of acoustic signals derived from a group of acoustic wave detecting elements to which approximately equal electrical noise is input among the plurality of acoustic wave detecting elements.

12. The object information acquiring apparatus according to claim 1, further comprising a recording unit on which an electrical signal derived from the electrical noise and acquired in advance is recorded as a recorded electrical signal, wherein the noise reducer adjusts a phase and an amplitude of the reference signal using the recorded electrical signal.

13. The object information acquiring apparatus according to claim 1, wherein the acoustic wave is a photoacoustic wave generated from the object irradiated with light.

14. The object information acquiring apparatus according to claim 1, wherein the acoustic wave is a reflected wave which is transmitted to the object and subsequently reflected inside the object.

15. The object information acquiring apparatus according to claim 1, wherein the acoustic wave detecting element and the reference element are provided in proximity to each other.

16. The object information acquiring apparatus according to claim 1 further comprising:

a difference processor which performs difference processing on a pair of electrical signals output from a pair of the acoustic wave detecting elements and the reference element.

17. The object information acquiring apparatus according to claim 16, wherein sensitivity of the reference element with respect to the acoustic wave is approximately zero.

18. The object information acquiring apparatus according to claim 16, wherein the pair of the acoustic wave detecting elements and the reference element are provided in proximity to each other.

19. The object information acquiring apparatus according to claim 16, comprising a plurality of pairs of the acoustic wave detecting elements and the reference element.

* * * * *